United States Patent
Kaye et al.

(10) Patent No.: US 9,784,387 B2
(45) Date of Patent: Oct. 10, 2017

(54) FLEXIBLE PLASTIC HOSE AND METHOD FOR MANUFACTURING SAME

(75) Inventors: Neil Kaye, Balmain (AU); Harry Wu, Dongguan (CN); Tyro Wang, Dongguan (CN)

(73) Assignee: PLASTIFLEX GROUP, Paal-Beringen (BE)

( * ) Notice: Subject to any disclaimer, the term of this patent is extended or adjusted under 35 U.S.C. 154(b) by 392 days.

(21) Appl. No.: 14/112,697

(22) PCT Filed: Apr. 23, 2012
(Under 37 CFR 1.47)

(86) PCT No.: PCT/EP2012/057396
§ 371 (c)(1),
(2), (4) Date: Nov. 12, 2013

(87) PCT Pub. No.: WO2012/143563
PCT Pub. Date: Oct. 26, 2012

(65) Prior Publication Data
US 2014/0053939 A1 Feb. 27, 2014

(30) Foreign Application Priority Data

Apr. 21, 2011 (EP) .................................. 11163335

(51) Int. Cl.

| | |
|---|---|
| *F16L 9/00* | (2006.01) |
| *F16L 11/00* | (2006.01) |
| *F16L 11/118* | (2006.01) |
| *A61M 39/12* | (2006.01) |
| *F16L 33/24* | (2006.01) |
| *F16L 33/34* | (2006.01) |
| *F16L 11/112* | (2006.01) |
| *F16L 35/00* | (2006.01) |

(52) U.S. Cl.
CPC .......... *F16L 11/1185* (2013.01); *A61M 39/12* (2013.01); *F16L 11/112* (2013.01); *F16L 33/24* (2013.01); *F16L 33/34* (2013.01); *F16L 35/00* (2013.01); *A61M 2205/0216* (2013.01); *F04C 2270/0421* (2013.01)

(58) Field of Classification Search
CPC ............................ F16L 11/112; F16L 11/1185
USPC ................................................ 138/109, 96 T
See application file for complete search history.

(56) References Cited

U.S. PATENT DOCUMENTS

| 3,008,738 A | 11/1961 | Longfellow | |
|---|---|---|---|
| 3,127,227 A * | 3/1964 | Edwards | A47L 9/246 439/195 |
| 3,928,715 A * | 12/1975 | Holden | A47L 9/246 138/103 |

(Continued)

FOREIGN PATENT DOCUMENTS

| DE | 196 40 742 A1 | 4/1998 |
|---|---|---|
| GB | 2 065 823 A | 7/1981 |

*Primary Examiner* — Vishal Pancholi
(74) *Attorney, Agent, or Firm* — Sughrue Mion, PLLC (57) ABSTRACT

Disclosed is a flexible plastic hose (1) comprising a tubular hose body (2) having web portions (7) and a helical reinforcing rib (8), and a cuff (3*a*) mounted to an extremity (16) of the hose body (2) comprising a molded end fitting (5*a*) bonded to the extremity (16*a*), and a stress relief element (4) with a first segment (S1) having an internal screw-thread (15) complementary to the helical reinforcing rib (8). Disclosed is also a method for making same, and use of the hose (1) as a medical hose.

21 Claims, 6 Drawing Sheets

(56) References Cited

U.S. PATENT DOCUMENTS

| | | | | |
|---|---|---|---|---|
| 3,934,902 | A * | 1/1976 | McNamee | F16L 25/0036 174/75 C |
| 4,063,790 | A * | 12/1977 | Kleykamp | A47L 9/2868 439/191 |
| 4,162,370 | A * | 7/1979 | Dunn | F16L 11/1185 138/122 |
| 4,277,640 | A * | 7/1981 | Kutnyak | A47L 9/246 174/47 |
| 4,345,805 | A * | 8/1982 | Finley | A47L 9/242 285/110 |
| 4,437,691 | A * | 3/1984 | Laney | F16L 25/0036 285/331 |
| 4,462,649 | A * | 7/1984 | Medford | F16L 33/32 174/47 |
| 6,099,046 | A * | 8/2000 | Oh | F16L 25/0036 285/353 |
| 6,733,315 | B2 * | 5/2004 | Linhart | A47L 9/246 439/191 |
| 6,877,781 | B2 * | 4/2005 | Edler | F16L 25/0036 285/322 |
| 7,100,950 | B2 * | 9/2006 | Martin | F16L 25/0045 285/319 |
| 7,690,695 | B2 * | 4/2010 | Duquette | F16L 25/0036 285/249 |
| 2003/0062722 | A1 * | 4/2003 | Linhart | F16L 37/0985 285/319 |

* cited by examiner

FLEXIBLE PLASTIC HOSE AND METHOD FOR MANUFACTURING SAME

CROSS REFERENCE TO RELATED APPLICATIONS

This application is a National Stage of International Application No. PCT/EP2012/057396 filed Apr. 23, 2012, claiming priority based on European Patent Application No. 11163335.0 filed Apr. 21, 2011, the contents of all of which are incorporated herein by reference in their entirety.

TECHNICAL FIELD

The invention relates to a flexible plastic hose according to the preamble of the first claim, and to a method for manufacturing such a flexible plastic hose.

BACKGROUND ART

A known hose comprises a flexible hose body having an outer wall with a reinforcing rib extending helically around the outer wall, the rib containing one or more electrical conductors. These electrical conductors are connected to an interface which is provided in one of the cuffs which are provided on the extremities of the hose body. The connector cuffs are manufactured onto the extremities of the hose body by moulding the cuff material directly onto the extremities. It has been found that the outer wall of the flexible hose body can be easily damaged at the transition point between the flexible hose body and the connector cuffs, when the hose is bent and/or pulled.

DISCLOSURE OF THE INVENTION

It is an object of the present invention to provide a flexible plastic hose that is able to resist a higher bending and pulling force exerted between its end fittings.

This object is achieved according to the present invention with a flexible plastic hose having all the technical characteristics of the first independent claim.

Thereto the flexible plastic hose according to the present invention comprises:

a hose body having a flexible tubular outer wall comprising web portions alternating with reinforcing rib portions of at least one helical reinforcing rib, the web portions having predetermined properties chosen for providing flexibility to the hose body, and the at least one reinforcing rib having predetermined properties for providing crush resistance to the hose body;

a cuff mounted to at least a first extremity of the hose body and comprising a moulded end fitting having a bore for connecting the hose to another device, the end fitting being bonded to the first extremity of the hose body;

whereby the cuff further comprises a stress relief element located at an entrance side of the cuff where the hose body enters the cuff, the stress relief element having a first segment with an internal screw-thread complementary to the helical reinforcing rib for closely fitting around the hose body without being bonded to the first extremity of the hose body, thereby reducing stress exerted on the web portions at the first extremity during use of the hose.

By providing a cuff comprising a stress relief element having a first segment with an internal screw thread complementary to the helical reinforcing rib, and by bonding the hose body to the cuff not at its entrance position but at the hose extremity being located beyond the stress relief element, the stress relief element actually encloses the hose body without being bonded thereto, allowing some freedom of movement of the hose body therein. The inventor found that this stress relief element allows forces exerted upon the hose body (during use) to be distributed over a larger contact area of the hose body, thereby avoiding or reducing stress concentrations in the hose body, in particular in its web portions.

In the cuff of the present invention, the stress relief element encloses the hose body without being secured thereto, and the securing of the hose body to the cuff only happens at the moulded end fitting, i.e. a distance from the entrance side of the cuff. Apparently in this way the forces exerted upon the hose body are spread over a larger area of the hose body, and the remaining forces exerted upon the hose extremities are reduced, so that the hose can withstand higher external bending and pulling forces.

Preferably the stress relief element further comprises a second, substantially cylindrical segment at the entrance side of the cuff, having an inner diameter provided for closely fitting around the reinforcing rib in axial direction but allowing flexibility of the hose body in its longitudinal direction.

This thread-less second segment of the stress relief element allows even more movement of the hose body within the stress relief element. In particular it allows movement in longitudinal direction of the cuff without rubbing of the hose. The inventor found that this cylindrical segment seems especially advantageous when bending forces are applied to the hose, probably due to the fact that the cylindrical segment allows a higher degree of deformation of the hose body outside of the threaded segment. Thus the cylindrical segment of the stress relief element allows an even further reduction of the stress exerted upon the hose body, in particular on the web portions.

Preferably the stress relief element further comprises a first and a second substantially cylindrical outer surface having a first resp. second outer diameter, the first cylindrical outer surface being provided for being overmoulded with the material of the moulded end fitting, which increases the bonding area between the moulded end fitting and the stress relief element.

A larger bonding area improves the connection of the moulded end fitting to the stress relieve element screwed around the hose body, to obtain a rigid cuff.

The first and/or the second outer surface of the stress relief element do not necessarily need to be substantially cylindrical in shape, as long as the effect of an increased bonding area is provided. The surface may for instance also be conical or elliptical.

The connection of the cuff to the hose does not necessarily need to be achieved by overmoulding, as long as the connection responds to the desired properties, such as the mechanical properties and/or an acceptable isolation of the inside of the hose from the outside environment of the hose. Any other suitable process for connecting the cuff to the hose may be used, such as for instance through spin welding, or by screwing.

Preferably the first cylindrical outer surface further comprises protrusions and/or recessions for also providing a mechanical lock between the moulded end fitting and the stress relief element.

When overmoulding the stress relief element for forming the cuff, these protrusions and/or recessions provide for an improved mechanical grip between the end fitting and the stress relief element.

Preferably the internal screw thread extends over at least half a winding of the helical reinforcing rib, preferably at least one winding, more preferably at least two windings.

It has been found that half a winding can be sufficient, but a full or multiple windings allow for an even better stress reduction. When the hose is pulled or bent, the stress relief element allows the stress to be distributed over several windings of the reinforcing rib, rather than at one stress concentration point. This substantially reduces the risk of failure of the hose at the joint between the cuff and the hose body.

It is a further object of the present invention to provide a method for manufacturing such a flexible plastic hose. This further object is achieved with the manufacturing method of the second independent claim.

Thereto the method of the present invention comprises the following steps:

a) providing a hose body having a flexible tubular outer wall comprising web portions alternating with reinforcing rib portions of at least one helical reinforcing rib, the web portions having predetermined properties chosen for providing flexibility to the hose body and the at least one reinforcing rib having predetermined properties for providing crush resistance to the hose body;

b) providing a stress relief element having a first segment with an internal screw thread complementary to the helical reinforcing rib and provided for closely fitting around the hose body (2);

c) screwing the stress relief element on a first extremity of the hose body, such that the helical reinforcement rib is engaged in the internal thread of the stress relief element, and in such a way that the first extremity of the hose body extends beyond the stress relief element;

d) moulding or spin welding an end fitting having a bore onto the extremity of the hose body and over part of the stress relief element, such that the end fitting is bonded to the extremity and the stress relief element.

In other words, the stress relief element, which is designed to match dimensions of the supporting rib of the hose body, is screwed onto the hose body prior to moulding the cuff onto the hose body. As the stress relief element is not directly bonded to the hose body, the step of bonding (e.g. gluing the hose body can be omitted. Next, the stress relief element itself is bonded to the cuff by partly overmoulding it, thereby forming the cuff.

BRIEF DESCRIPTION OF THE DRAWINGS

The invention will be further elucidated by means of the following description and the appended drawings.

DETAILED DESCRIPTION OF PREFERRED EMBODIMENTS

References 1 hose
2 body
3 cuff
4 stress relief element
5 end fitting
6 wire exit
7 web
8 helical rib
9 electrical wire
10 recess
11 first shoulder
12 second shoulder
13 protrusions (or recessions)
14 bore
15 internal screw thread
16 extremity
18 electrical interface
19 entrance side of cuff
20 first cylindrical outer surface
21 second cylindrical outer surface
p pitch The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Crush resistance is the resistance a hose provides against collapsing of the hose under lateral pressure, such as when one would stand on a hose laying on the floor. Crush resistance may also be called hub strength or hoop strength, and is an important feature for a flexible hose in many of its applications.

Flexible hoses for connection between two devices are known in the art, for example for connecting a vacuum cleaner to a cleaning brush, or for connecting a medical breathing device to a mouth-piece, but the invention is not restricted thereto, and can also be used for other hoses. The hoses typically have a ribbed flexible tubular body, and a cuff mounted at each end of the tubular body, for connecting the hose to external devices.

Different ways of mounting the cuff are known in the art. In one such embodiment the cuff is directly moulded on the tubular hose, which provides for a tight connection, but has the disadvantage of showing stress concentration at the location where the tubular hose body enters the cuff, which will ultimately break when the hose is subjected to bending or pulling forces during use of the hose.

The flexible hose shown in the drawings is better able to withstand such bending or pulling forces.

Figure 1:
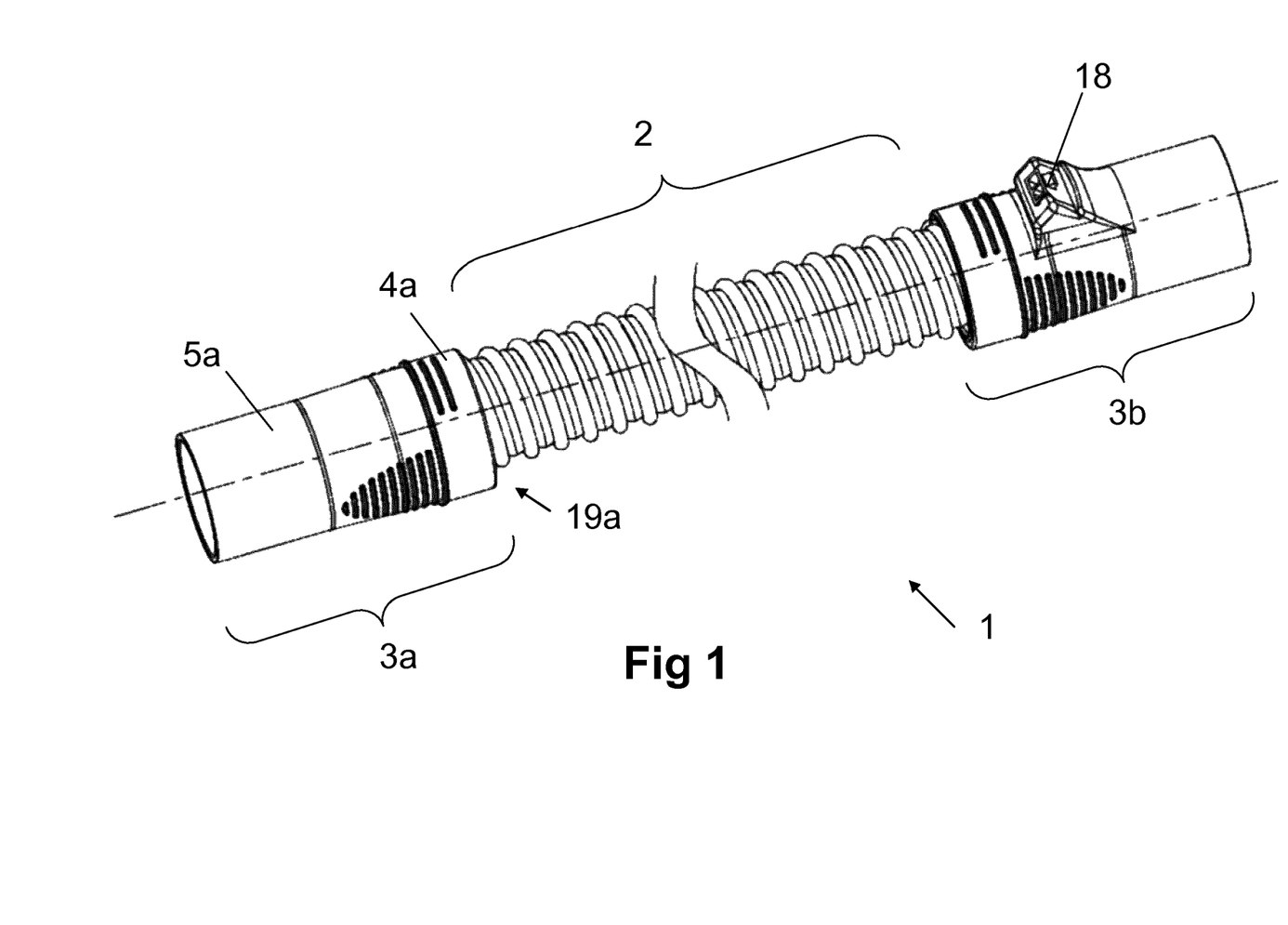
FIG. 1 shows a perspective view of a preferred embodiment of the flexible plastic hose according to the present invention.

FIG. 1 shows a preferred embodiment of the hose 1 according to the present invention. The flexible plastic hose 1 comprises:

a hose body 2 having a flexible tubular outer wall comprising web portions 7 alternating with reinforcing rib portions of at least one helical reinforcing rib 8, the web portions 7 having predetermined properties chosen for providing flexibility to the hose body 2 and the at least one reinforcing rib 8 having predetermined properties for providing sufficient crush resistance to the hose body 1 (i.e. for preventing it from collapsing and for making it capable to withstand pressure exerted on the outer wall of the hose and upon release of the pressure, returning the outer wall to the original shape—required crush resistance depends on the application);

a cuff 3a mounted to a first extremity of the hose body 2 and comprising a moulded end fitting 5a having a bore 14 for connecting the hose 1 to another device, the end fitting 5a being bonded to the first extremity 16a of the hose body 2;

the cuff 3 further comprises a stress relief element 4 located at an entrance side 19 of the cuff 3 where the hose body 2 enters the cuff 3, the stress relief element 4 having a first segment S1 with an internal screw-thread 15 complementary to the helical reinforcing rib 8 for closely fitting around the hose body 2 without being bonded to the first extremity 16a of the hose body 2, thereby reducing stress exerted on the web portions 7 at the first extremity 16 during use of the hose 1.

The hose according to the present invention has a separate stress relief element 4 which is designed to match dimensions of the supporting rib 8 of the hose body 2. The stress relief element 4 is screwed onto the hose body 2 prior to moulding the cuff 3 onto the hose body 2. The stress relief element 4 fits closely around the hose body 2 but is not directly bonded to the hose body 2, which allows the hose body 2 to move slightly within the stress relief element 4. The stress relief element 4 is over-moulded when the cuff 3 is moulded onto the hose body 2 and therefore becomes bonded with the cuff 3. When the hose body 2 is pulled or bent with the stress relief element 4 in place, the stress is distributed over several pitches of the helical rib 8, rather than at one stress concentration point. This reduces the risk of failure of the hose body 2 at the joint between the cuff 3 and the hose body 2.

The stress relief element 4 acts as a rigid sleeve to lock the tubular hose body 2 in place. When an external bending or pulling force is applied to the hose body 2, the internal screw-thread restricts the bending or stretching of the part of the hose body which it holds.

The hose shown in FIG. 1 has a flexible hollow tubular body 2 of a desired length, depending on the application. The hose body 2 preferably has a relatively thin web (e.g. 1.0 mm thick), which is reinforced by a helical rib 8 extending over the entire length of the flexible body 2. Several methods for manufacturing such a tubular body are described in the art, for example in one embodiment the webs 7 and ribs 8 may be coextruded and subsequently wound on a mandrel, in a way as described in U.S. Pat. No. 4,162,370. As this is not the focus of the present invention, no further explanation is deemed necessary here.

The at least one helical reinforcing rib 8 has predetermined properties (e.g. thickness, material, pitch, etc) for providing sufficient mechanical strength and stiffness to the hose body 2. In a preferred embodiment the helical rib 8 comprises polypropylene surrounded by polyolefin. In another preferred embodiment the helical rib 8 comprises polyethylene surrounded by polyolefin, but other materials may also be used. In an embodiment, the rib comprises at least one material selected from the group consisting of: polypropylene, polyethylene, and any other material approved according to ISO 10993 for use in medical applications, preferably this material being surrounded by a coating comprising the same material as is used in the web, or a material compatible therewith. This material selection enhances the adhesion between the rib and the web.

The rib may e.g. have a substantially circular cross section with a diameter of e.g. 1.0-3.0 mm, or a substantially elliptical cross section with a width W of e.g 2.70 mm and a height T of e.g. 1.70 mm (FIG. 6), but other dimensions and other shapes may also be used. As the rib 8 is used as screw thread in the stress relief element 4, it should have at least 1.00 mm thickness for most consumer or medical applications.

Between the rib portions 8, the hose body 2 according to the present invention comprises web portions 7 having predetermined properties (e.g. dimensions, material, etc) chosen for providing desired flexibility to the hose body 2. In a preferred embodiment of the hose according to the present invention, the width of the web portions 7 between two successive rib portions 8 is 1.0-10.0 mm, more preferably 6.0-7.0 mm. In an example the hose has a single helical rib 8, and the pitch of that helix is substantially 6.4 mm.

Figure 4:
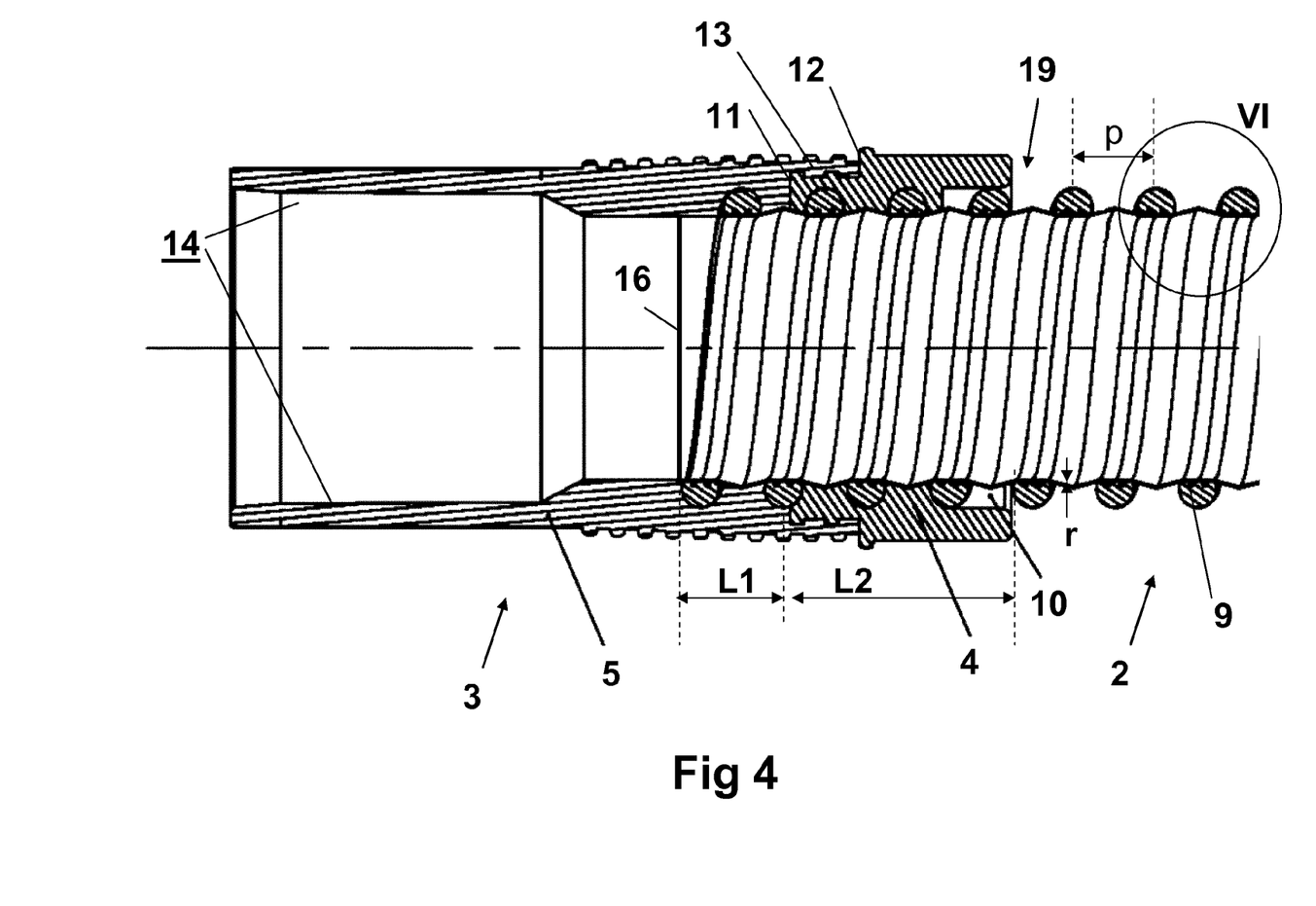
FIG. 4 shows in more detail the cuff of the hose of FIG. 3.

In an embodiment, the pitch p of the reinforcing ribs of the flexible plastic hose according to the present invention is preferably in the range of 3.0 to 9.0 mm, more preferably 4.0 to 8.0 mm, even more preferably 5.0 to 7.0 mm, and most preferably about 6.2 mm. The pitch is conventionally measured as shown in FIG. 4 from the top of one rib to the top of the adjacent rib.

In another embodiment according to the present invention, the ribs have a width of at least 0.05 mm [IS THIS OK, OR SHOULD IT BE 0.5 MM?], preferably at least 1.0 mm, more preferably at least 1.5 mm, optionally at most 4.0 mm, preferably at most 3.0 mm, more preferably at most 2.5 mm, even more preferably at most 2.0 mm, and typically 1.7±0.2 mm.

In yet another embodiment according to the present invention, the rib has a height of at least 0.05 mm, preferably at least 0.05 mm [IS THIS OK, OR SHOULD IT BE 0.5 MM?], preferably at least 1.0 mm, more preferably at least 2.0 mm, optionally at most 5.0 mm, preferably at most 4.0 mm, more preferably at most 3.5 mm, even more preferably at most 3.0 mm and typically 2.7±0.2 mm.

The width of the web portions 7 should be at least 1.0 mm between the rib portions 8 in order to provide sufficient flexibility. The radial thickness of the web portions 7 of the hose 1 of the present invention is preferably 0.10-0.25 mm, more preferably 0.16-0.22 mm. This allows for a very flexible hose, which can easily bend over 90° under a weight of e.g. 0.100 kg or 0.200 kg. Optionally the web is transparent, so that flow of the fluid (gas or liquid) inside the tube may be visible. Preferably the web portions 7 are made of a material chosen from the group consisting of: polyolefin, metallocene PE, polyvinylchloride (PVC), preferably flexible PVC, and any other material approved according to ISO 10993 for use in medical applications.

The hose of FIG. 1 has at its both ends a first and a second cuff 3a, 3b, but the hose of the present invention may only comprise a single cuff 3. Apart from the electrical interface 18, which is not the focus of the present invention, both cuffs 3a, 3b of FIG. 1 are substantially identical, and therefore only one will be described in detail further.

Figure 2:
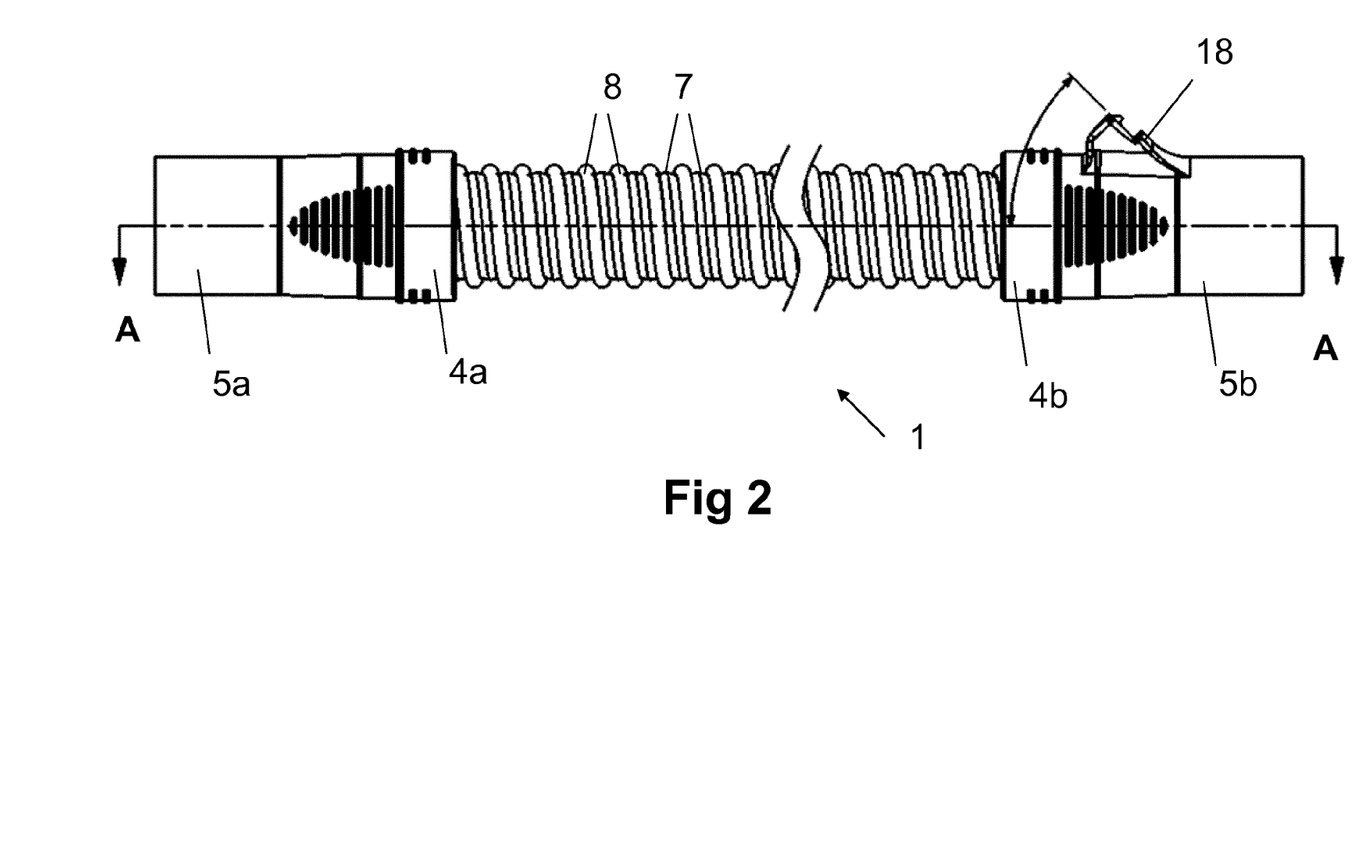
FIG. 2 shows the hose of FIG. 1 in side view.

FIG. 2 shows the hose 1 of FIG. 1 in side view.

Figure 3:
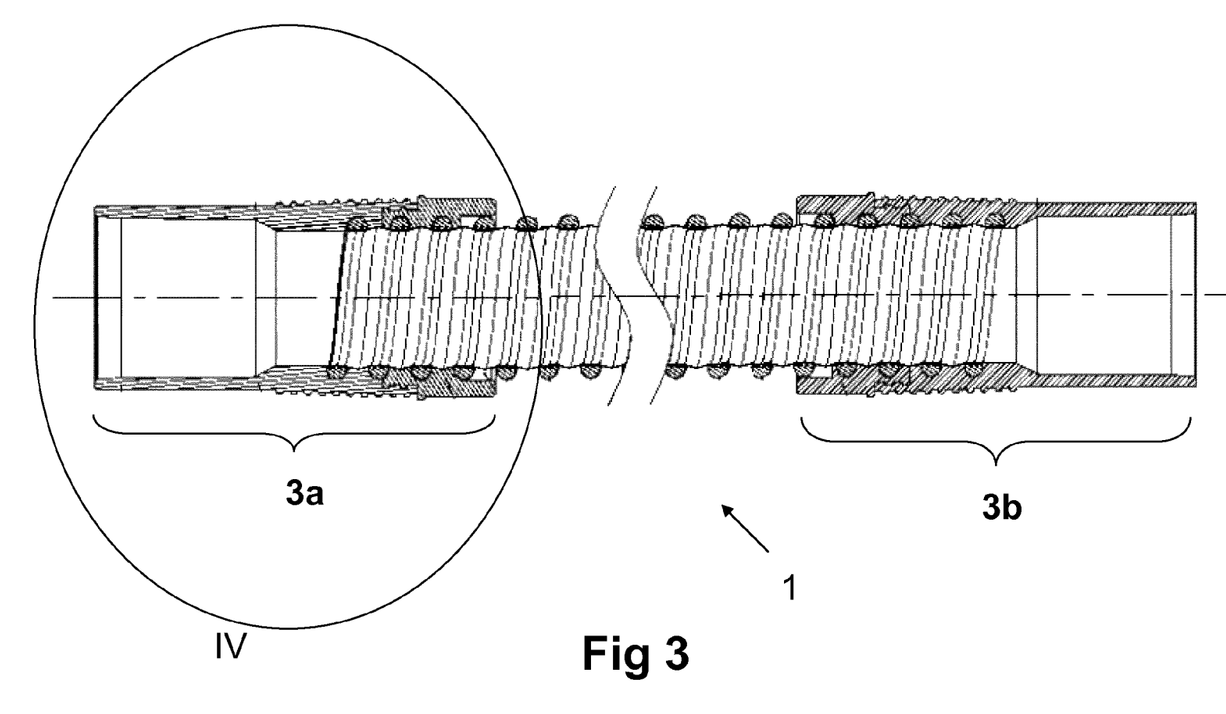
FIG. 3 shows the hose of FIG. 2 in cross-section along line A-A.

FIG. 3 shows the hose 1 of FIG. 2 in cross-section along line A-A. As can be seen, the cuff 3a, 3b are substantially identical, therefore only one of them will be described further.

FIG. 4 shows a preferred embodiment of the cuff 3 of the hose 1 of the present invention, and its connection with the hose body 2 in more detail. During manufacture of the hose 1, first a stress relief element 4 is screwed on the hose body 2, in such a way that part of the hose body 2 extends beyond the stress relief element 4 (distance L1), and then an end fitting 5 is applied by over-moulding the hose body 2 and at least part of the stress relief element 4. The resulting cuff 3 then comprises two parts: an end fitting 5 located at and bonded to the extremity 16 of the hose body 2, and a stress relief element 4 located between the end fitting 5 and the entrance 19 of the cuff 3 where the hose body 2 enters the cuff 3. The stress relief element 4 has a first segment S1 (see also FIG. 5) with an internal screw-thread 15 for receiving the complementary helical reinforcing rib 8 for closely fitting around the hose body 2 without being bonded the helical rib 8 (e.g. by gluing) to the stress relief element 4. By not bonding the hose body 2 to the stress relief element 4 directly, but allowing some movement therein, a larger part of the hose body 2 (in particular the enforcing rib 8) contributes for counteracting any external forces, in particular bending forces and/or pulling forces exerted upon the hose body 2. This effectively lowers the force (and corresponding stress) exerted upon the part of the hose body 2 bonded in the end fitting 5, thereby reducing the risk of damaging the hose 1, in particular the web portions 7.

The end fitting 5 typically has a bore 14, (e.g. a cylindrical or conical bore) for connecting the hose 1 to an external device, e.g. a respiratory device (not shown) on one side of the hose 1, and a mouth piece (not shown) on the other side.

In a preferred embodiment of the flexible plastic hose 1 according to the present invention, the stress relief element 4 further comprises a second, substantially cylindrical segment S2 (see FIG. 4 and FIG. 5) at the entrance side 19 of the cuff 3, having an inner diameter d3 provided for closely fitting around the helical reinforcing rib 8 in axial direction, but allowing flexibility of the hose body 2 in its longitudinal direction. This second segment of the stress relief element 4, without screw-thread, allows the hose body 2 to move within the stress relief element without rubbing of the hose body. Tests have shown that this second segment S2 is particularly useful to counteract bending forces, as it allows the hose body 2 to slightly deform already in the cylindrical part S2, without forcing the ribs in an enclosure. This further reduces the stress concentration exerted upon the extremity 16.

Figure 5:
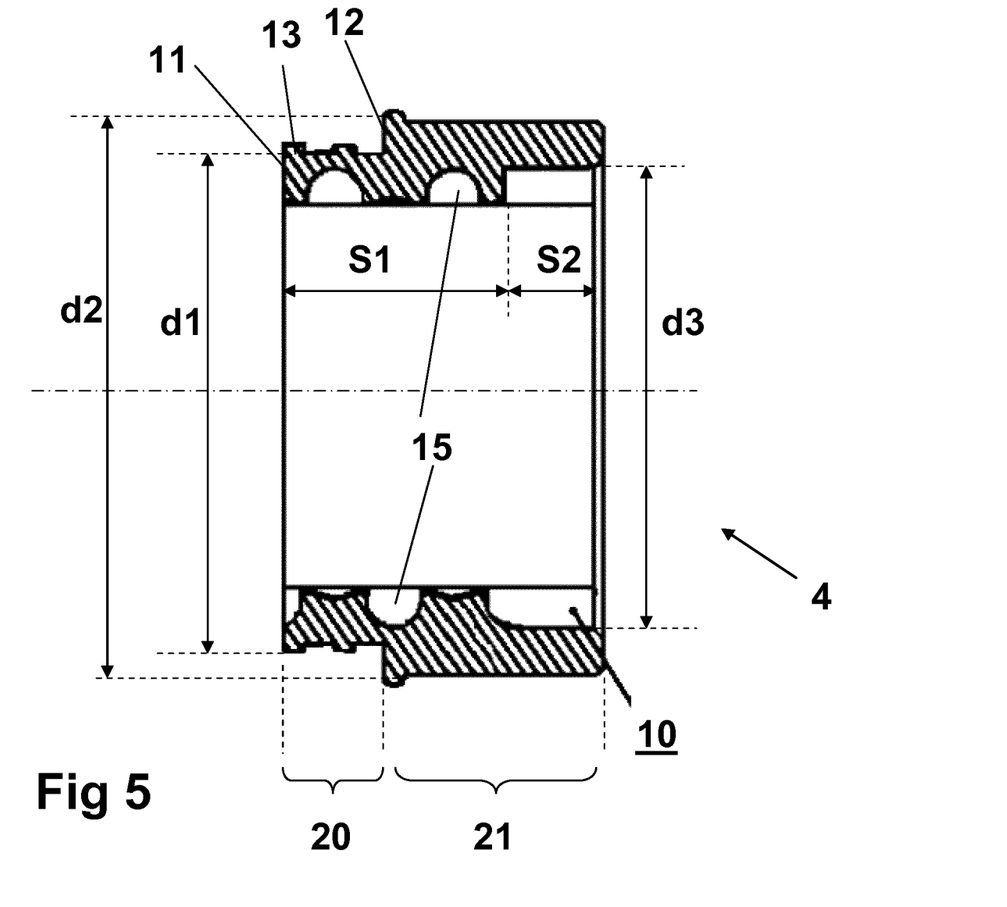
FIG. 5 shows in more detail the stress relief element of the cuff of FIG. 4.

In the preferred embodiment of the hose 1 according to the invention, the stress relief element 4 further comprises a first and a second substantially cylindrical outer surface 20, 21 having a first resp. second outer diameter d1, d2, the first cylindrical outer surface 20 being provided for overmoulding for increasing the bonding area between the moulded end fitting 5a and the stress relief element 4, as shown in FIG. 4 and FIG. 5. The first cylindrical outer surface extends between the first shoulder 11 and the second shoulder 12. The larger the distance between the first and second shoulders 11 and 12, the larger the first substantially cylindrical area becomes, and the larger the bonding becomes between the end fitting 5 and the stress relief part 4. Alternatively the end fitting 5 could have been overmoulded over the entire stress relief part 4, but this would result in a larger outer diameter of the cuff 3, which is not desirable.

Preferably the first cylindrical outer surface 20 further comprises protrusions 13 and/or recessions (not shown) for also providing a mechanical connection between the moulded end fitting 5 and the stress relief element 4. Such protrusions may e.g. take the form of teeth, or a flange at the shoulder edge, but also other techniques may be used. For example, the roughness of the first outer surface 20 could also be increased by sandblasting.

Preferably the size of the first segment S1 of the stress relief element 4 is chosen such that the internal screw thread 15 of the stress release element 4 extends over at least half a winding of the helical reinforcing rib 8, preferably at least one winding, more preferably at least two windings, so that when the hose is pulled or bent, the stress relief element 4 allows the stress exerted upon the hose body 2 to be distributed over several pitches of the enforcing rib 8, rather than at one stress concentration point. This reduces the risk of damage to the hose 1 under bending and/or pulling forces. In general, the more windings, the lower the stress, and the higher the external forces may be before damage occurs. The person skilled in the art can find a suitable number of windings by carrying out routine tests. The minimum of half a winding applies especially to a hose with a double-helix rib 8. The minimum of one winding applies especially to a hose with a single helix rib 8.

The size of the second segment S2 is preferably at least one pitch p of the hose.

The end fitting 5 preferably comprises a material selected from the group of polypropylene, polyethylene, polyester and any other material approved according to ISO 10993 for use in medical applications. Preferably the cuff 3 is made of the same material as the rib 8, so that good cohesion of the end fitting 5 and the hose body extending the stress relief element 4 can be achieved. Alternatively the cuff 3 may be made of polyolefin. In case of polyester, Hitrel® has been found very suitable.

Figure 6:
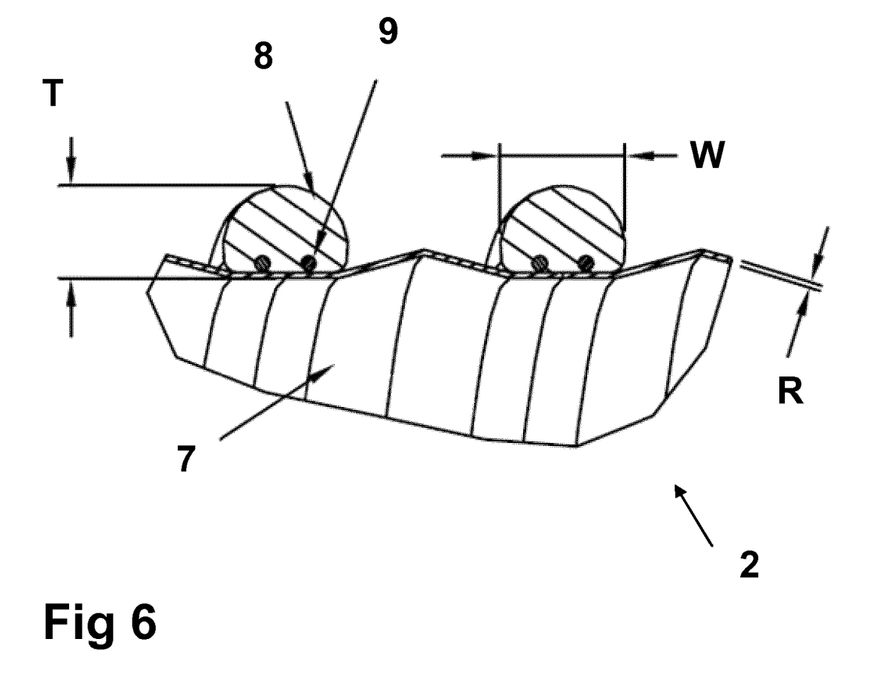
FIG. 6 shows in more detail part of the hose body of FIG. 4.

FIG. 6 shows part of the hose body 2 of FIG. 4 in more detail. Optionally at least one electrical wire 9 is integrated into the outer wall of the hose body 2, the electrical wire 9 preferably being located inside and being isolated by the reinforcing ribs 8. In FIG. 6 two electrical wires are integrated in the helical enforcing rib 8. In an embodiment the wires are copper wires, having a diameter of substantially 0.29 mm, but other dimensions and other materials may also be used. If one or more electrical wires 9 are present, they are preferably connected to an electrical interface 18 integrated in the end fitting 5 of the cuff 3, as shown in FIG. 1 or FIG. 2. The electrical wire 9 may be a heating resistance, a communication wire or both.

The flexible plastic hose 1 described above, may be used advantageously as a medical hose, provided that plastic materials suitable for medical purposes are used, more preferably materials approved according to ISO 10993 for use in medical applications.

In a particular use, the hose 1 is a medical hose comprising at least one electrical wire, integrated into the outer wall of the hose body 2, preferably being located inside and isolated by the reinforcing ribs 8, but possibly alternatively in the web or in the weld, and being used for instance for a purpose selected from (i) warming up a fluid (gas and/or liquid) inside the hose body 2, (ii) as a temperature sensor, (iii) as a humidity sensor, (iv) as a sensor for the presence of any chemical component such as e.g. oxygen and/or carbon dioxide presence, and (v) for any other type of sensor, as well as for electrically connecting to a heating device or a sensor. In this case, in particular for heating, the heating wire may be made accessible for electric power via an interface 18 in the cuff 3 which may be moulded onto the extremity of the hose body 2. The electrical wire may comprise any electrically conductive material, such as a metal, preferably copper but also aluminium, gold or silver would be very suitable. Also any conductive plastic compound may be suitable.

The hose 1 of the present invention may for example be used in a respiratory device such as a CPAP (Continuous Positive Airway Pressure) device.

For example, the corrugated outer surface may be implemented by folded web portions 7. Instead of having only one helical rib 8, the flexible body 2 may also have multiple helical ribs 8, for example two or more.

In an embodiment the hose further comprises a heating element, preferably a co-axial cable construction which extends in longitudinal direction of the hose body 2, the cable construction comprising two electrical wires 9, one of which being a heating wire and the other being provided for feedback purposes, the two electrical wires 9 being separated by a negative temperature coefficient (NTC) component. Such a co-axial cable construction has the advantage that it has a very small diameter, so that it can be associated with the hose in a number of different ways, such as for instance in a rib 8 in the wall of the hose, in a wire groove at the inside of the hose 2 or the outside of the hose, wound like a spring.

The pitch p of the helical ribs 8 may be constant or may vary in longitudinal direction of the hose 1. The latter is for instance done in case a heater wire is inserted and an intensive heating is for instance desired in the centre of the hose and a less intensive heating is desired near the edges of the hose 1. Each of the helical ribs 8 may be provided for carrying one or more wires 9. Some of the ribs 8 may not carry any wires. Different ribs 8 may also differ in width and height, depending of the type and number of wires 9 to be carried. The conduit may comprise more than two helical ribs.

FIG. 1 shows an electrical interface 18 at one end, but in an alternative embodiment an interface 18 is provided at both ends.

The invention claimed is:

1. A flexible plastic hose comprising:
a hose body having a flexible tubular outer wall comprising web portions alternating with reinforcing rib portions of at least one helical reinforcing rib, the web portions having predetermined properties chosen for providing flexibility to the hose body and the at least one reinforcing rib having predetermined properties for providing crush resistance to the hose body; and
a cuff mounted to at least a first extremity of the hose body and comprising:
a stress relief element located at an entrance side of the cuff where the hose body enters the cuff, the stress relief element having a first segment with an internal screw-thread complementary to the helical reinforcing rib for and closely fitting around the hose body without being bonded to the first extremity of the hose body, the stress relief element being for reducing stress exerted on the web portions at the first extremity during use of the hose, wherein the stress relief element is screwed onto the first extremity of the hose body such that a portion of the first extremity of the hose body extends beyond the stress relief element; and
a moulded end fitting having a bore for connecting the hose to another device, the end fitting being integrally moulded on the first extremity of the hose body and over part of the stress relief element and being bonded to said part of the stress relief element and said portion of the first extremity of the hose body.

2. The flexible plastic hose according to claim 1, wherein the stress relief element further comprises a second, substantially cylindrical segment without the internal screw-thread at the entrance side of the cuff, having an inner diameter provided for closely fitting around the reinforcing rib in axial direction but allowing flexibility of the hose body in its longitudinal direction.

3. The flexible plastic hose according to claim 1, wherein the stress relief element further comprises a first and a second substantially cylindrical outer surface having a first resp. second outer diameter, the first cylindrical outer surface being said part of the stress relief element over which the moulded end fitting is mounted and to which the moulded end fitting is bonded.

4. The flexible plastic hose according to claim 3, wherein the first cylindrical outer surface further comprises protrusions and/or recessions for also providing a mechanical lock between the moulded end fitting and the stress relief element.

5. The flexible plastic hose according to claim 1, wherein the internal screw thread of the stress relief element extends over at least half a winding of the helical reinforcing rib.

6. The flexible plastic hose according to claim 1, wherein the pitch of the rib or ribs is at least 3.0 mm.

7. The flexible plastic hose according to claim 1, wherein the wall thickness of the web portions is 0.10-0.25 mm.

8. The flexible plastic hose according to claim 1, wherein the web portions are made of a material chosen from the group comprising: polyolefin, metallocene PE, polyvinylchloride (PVC), flexible PVC, and any other material approved according to ISO 10993 for use in medical applications.

9. The flexible plastic hose according to claim 1, wherein the rib comprises at least one material selected from the group of: polypropylene, polyethylene, and any other material approved according to ISO 10993 for use in medical applications.

10. The flexible plastic hose according to claim 1, wherein the end fitting comprises a material selected from the group of: polypropylene, polyethylene, polyester and any other material approved according to ISO 10993 for use in medical applications.

11. The flexible plastic hose according to claim 1, wherein at least one electrical wire/cable is integrated into the outer wall of the hose body.

12. The flexible plastic hose according to claim 11, wherein the at least one electrical wire/cable is connected to an electrical interface integrated in the end fitting of the cuff.

13. A method of manufacturing a flexible plastic hose, comprising the steps of:
a) providing a hose body having a flexible tubular outer wall comprising web portions alternating with reinforcing rib portions of at least one helical reinforcing rib, the web portions having predetermined properties chosen for providing flexibility to the hose body and the at least one reinforcing rib having predetermined properties for providing crush resistance to the hose body;

b) providing a stress relief element having a first segment with an internal screw thread complementary to the helical reinforcing rib provided for closely fitting around the hose body;

c) screwing the stress relief element on a first extremity of the hose body, such that the at least one helical reinforcing rib is engaged in the internal thread of the stress relief element and the stress relief element closely fits around the first extremity without being bonded thereto, and in such a way that the extremity of the hose body extends beyond the stress relief element;

d) integrally moulding or spin welding an end fitting having a bore onto the first extremity of the hose body and over part of the stress relief element, such that the end fitting is bonded to the first extremity and the stress relief element.

14. The flexible plastic hose according to claim 1, wherein the hose is manufactured in predetermined plastic materials suitable for medical purposes.

15. The flexible plastic hose according to claim 14, wherein at least one electrical wire is integrated into the outer wall of the hose body, the electrical wire preferably being located inside and isolated by the reinforcing ribs, and being provided for a purpose or use selected from (i) warming up a fluid inside the hose body, (ii) as a temperature sensor, (iii) as a humidity sensor, (iv) as a sensor for oxygen, carbon dioxide presence, and (v) for any other type of sensor.

16. The flexible plastic hose according to claim 1, wherein the internal screw thread of the stress relief element extends over at least one winding of the helical reinforcing rib.

17. The flexible plastic hose according to claim 1, wherein the internal screw thread of the stress relief element extends over at least two windings of the helical reinforcing rib.

18. The flexible plastic hose according to claim 1, wherein the pitch of the rib or ribs is at least 5.0 mm.

19. The flexible plastic hose according to claim 1, wherein the wall thickness of the web portions is 0.16-0.22 mm.

20. The flexible plastic hose according to claim 9, wherein the rib is surrounded by a coating comprising the same material as is used in the web, or a material compatible therewith.

21. The flexible plastic hose according to claim 1, wherein at least one electrical wire/cable is integrated into the outer wall of the hose body, the electrical wire/cable being integrated in the reinforcing ribs or in the web.

* * * * *